(12) United States Patent
Walter et al.

(10) Patent No.: US 8,303,542 B2
(45) Date of Patent: Nov. 6, 2012

(54) OPHTHALMIC SURGICAL CASSETTE AND SYSTEM

(75) Inventors: Jonathan T. Walter, Wake Forest, NC (US); Mike Askew, Garner, NC (US)

(73) Assignee: Bausch & Lomb Incorporated, Rochester, NY (US)

( * ) Notice: Subject to any disclaimer, the term of this patent is extended or adjusted under 35 U.S.C. 154(b) by 1343 days.

(21) Appl. No.: 11/758,048

(22) Filed: Jun. 5, 2007

(65) Prior Publication Data

US 2007/0287959 A1 Dec. 13, 2007

(51) Int. Cl.
*A61M 37/00* (2006.01)
*F04B 43/08* (2006.01)
*F04B 43/12* (2006.01)
*F04B 45/06* (2006.01)

(52) U.S. Cl. ..................................... 604/131; 417/477.2
(58) Field of Classification Search ................ 604/131, 604/20, 22; 417/477.2–477.9, 477.11–477.13
See application file for complete search history.

(56) References Cited

U.S. PATENT DOCUMENTS

| | | | | |
|---|---|---|---|---|
| 4,493,695 A | * | 1/1985 | Cook | 604/27 |
| 4,626,248 A | * | 12/1986 | Scheller | 604/319 |
| 4,627,833 A | * | 12/1986 | Cook | 604/34 |
| 4,773,897 A | * | 9/1988 | Scheller et al. | 604/34 |
| 5,282,787 A | * | 2/1994 | Wortrich | 604/30 |
| 5,927,956 A | * | 7/1999 | Lim et al. | 417/477.13 |
| 6,024,428 A | * | 2/2000 | Uchikata | 347/7 |
| 6,511,454 B1 | * | 1/2003 | Nakao et al. | 604/31 |
| 7,238,010 B2 | * | 7/2007 | Hershberger et al. | 417/477.2 |
| 7,786,457 B2 | * | 8/2010 | Gao | 250/577 |
| 7,806,915 B2 | * | 10/2010 | Scott et al. | 607/106 |
| 2001/0035887 A1 | * | 11/2001 | Altfather et al. | 347/7 |

FOREIGN PATENT DOCUMENTS

WO WO 93/17729 9/1993

OTHER PUBLICATIONS

International Search Report (PCTISA/210) and Written Opinion (PCT/ISA/237) mailed on Apr. 16, 2008.

* cited by examiner

*Primary Examiner* — Kevin C Sirmons
*Assistant Examiner* — Andrew Gilbert
(74) *Attorney, Agent, or Firm* — Jeffrey Powers (57) ABSTRACT

A cassette 74 for use with an ophthalmic surgical pump 16 for collecting aspirant fluid and tissue from a patient's eye includes a rigid walled container 18 having an interior volume 42. At least one tapered alignment slot 20 is formed in a side wall of the container 18 and extends from a back wall 24 towards a front wall 26. An irrigation and aspiration manifold base 50 is removeably attached to the container 18. An aspiration path 46 is formed within the container 18 for receiving the aspiration fluid and the tissue from the eye and directing the flow of fluid towards a front half of the container 18 before the fluid and tissue collects within a majority of the interior volume 42 of the container 18. A fluid level indicator 34 is formed on a wall 22 of the container 18, such that an associated photo-detector 86 of the pump 16 may determine a level of fluid in the container 18.

15 Claims, 10 Drawing Sheets

OPHTHALMIC SURGICAL CASSETTE AND SYSTEM

BACKGROUND OF THE INVENTION

This application claims the benefit of Provisional Patent Application No. 60/812,378 filed Jun. 10, 2006 which is incorporated by reference herein.

1. Field of the Invention

The present invention is directed towards an ophthalmic surgical cassette and pump system. More specifically, the present application is directed to a venturi ophthalmic surgical cassette and pump.

2. Description of Related Art

Ophthalmic surgical cassettes for use with various pump systems, including venturi pumps are well known in the art. Such surgical cassettes, particularly for use with the venturi pump, typically include a rigid walled cassette that can be connected to irrigation/aspiration tubing. In turn, the tubing is typically attached to a surgical handpiece for use by a surgeon during eye surgery. The rigid walled cassettes then have a majority of an interior volume of a cassette or container that collects aspirant fluid and tissue flow from a surgical site for later disposal. Such cassettes may be disposable or reusable. Such rigid walled cassettes are typically held within a pump assembly and therefore, it is particularly important that such cassettes have a fluid level detection scheme to prevent the cassette from overflowing and leaking surgical fluids into the interior of the pump and creating a bio-hazard, as well as possibly damaging the pump.

There are known fluid level detection schemes, such as that found in U.S. Pat. No. 4,773,897, wherein a float ball is used within a defined chamber of the cassette. The float ball then floats with the increasing level of fluids within the cassette and eventually blocks the path between a lightsource and a photo-transistor, which combine to form a fluid level detector. Once the float ball blocks the path of light to the photo-detector, the system then triggers the pump to stop and aspiration ceases until the cassette is emptied. While such float ball schemes have been used for years and are reliable, over time the float balls become somewhat water logged and the precise amount of float from a ball can vary from ball-to-ball during manufacturing. Therefore, the precise level of fluids within a cassette is not consistently determined by such a float ball and light detector scheme.

It is common for pump cassettes to include aspiration and irrigation tubing attached to the cassette. This tubing typically has to be pulled off of mating barbs on the cassette when the cassette needs to be emptied. Pulling such tubing off the barbs can be somewhat difficult and time consuming and is not easily accomplished. Therefore, it would be desirable to have a collection cassette, wherein the majority of tubing does not have to be removed from its connections. This would speed-up surgery, and make it much more user friendly for operating room personnel to prepare the cassette for further surgery in a timely fashion.

Prior art surgical cassettes typically dump the fluid from the aspiration tube into the cassette at a position towards the rear of the cassette and away from the operator. During surgery, a surgical console typically has sensors and indicator icons and audible alerts for when aspiration flow is presumed to have ceased, while still applying a vacuum to the aspiration tubing. Such schemes generally are sufficient to allow safe operation of the surgical cassette. However, it would be desirable for an operator to easily see fluid flowing into the interior volume of the container of the cassette to provide easy and convenient visual feedback to the operator that aspiration fluid flow is present.

Typical prior art surgical cassettes are essentially a three-dimensional rectangle in shape. It would be desirable to provide some sort of alignment or insertion guides to assist the operator in properly inserting the cassette into its respective pump.

Therefore, there exists the need for an improved ophthalmic surgical cassette and system.

DETAILED DESCRIPTION OF THE PREFERRED EMBODIMENT

Figure 1:
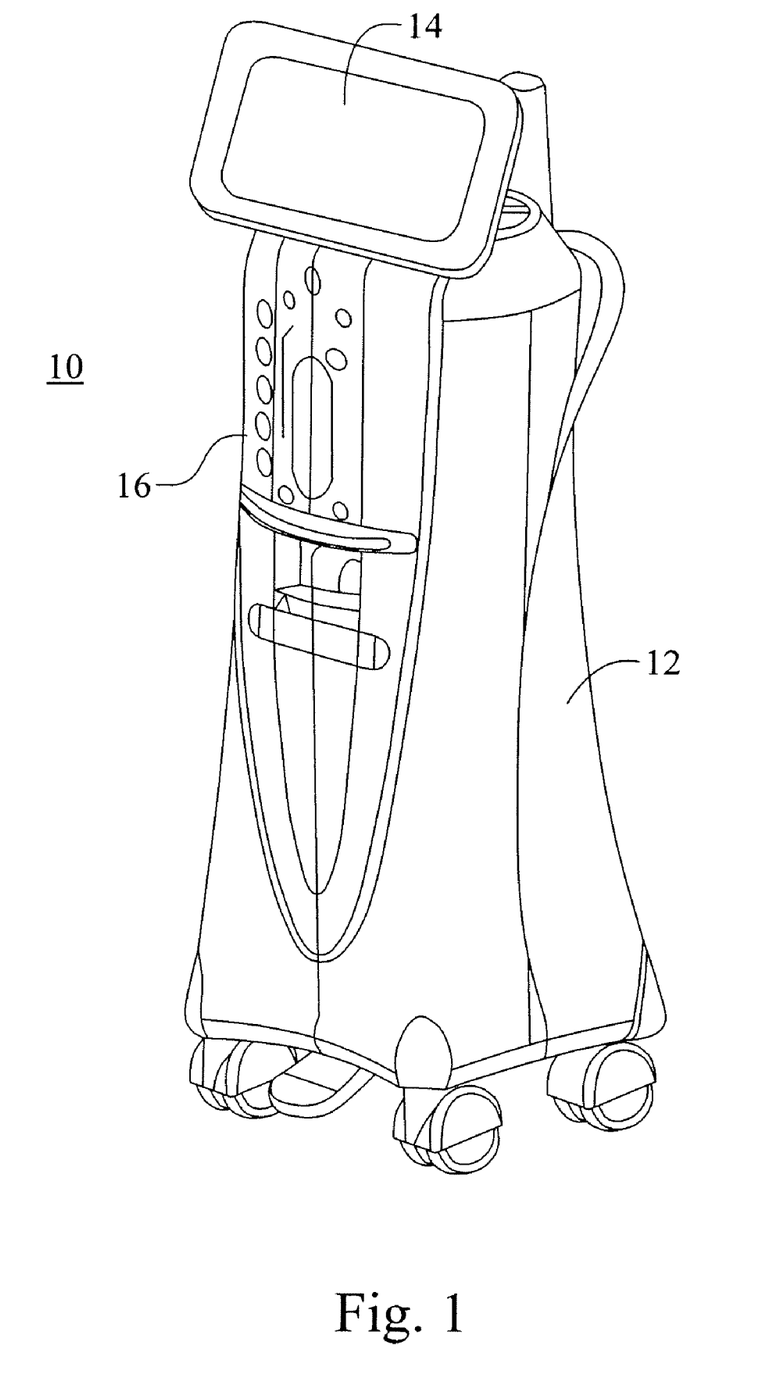
FIG. 1 is a perspective view of an ophthalmic surgical system in accordance with the present invention.

FIG. 1 shows a perspective view of an ophthalmic surgical console 10, in accordance with the present invention. Console 10 includes a body or chassis 12, a display 14, and a pump 16. Console 10 also may include an IV pole assembly, other ophthalmic surgical modules, such as a light module, scissors module, a second pump, and other typical ophthalmic surgical modules, all of which are not shown. A rigid walled container 18, with an interior volume described in detail below forms a part of a cassette for use with an ophthalmic surgery pump, such as pump 16, and is typically inserted into pump 16. The container is preferably formed of a transparent plastic material suitable for ophthalmic surgery, such as is well known in the art. Container or cassette 18 preferably includes at least one tapered alignment slot 20 formed in a side wall 22 of the container 18. The slot preferably extends from a back wall 24 towards a front wall 26. An irrigation manifold base (described in detail below), is preferably removeably attached to the container 18 and held on container 18 with barb 28 and notches 30. An aspiration path is preferably formed within the container 18 for receiving aspirant fluid and tissue from the eye through inlet 32. The aspiration path (described in detail below), preferably directs the flow of fluid towards a front half of the container before the fluid and tissue collects within a majority of the interior volume of the container 18. A fluid level indicator 34 is preferably formed on wall 22 of the container 18, such that an associated photo-detector of the pump (described in detail below) may determine a level of fluid in container 18.

Figure 2:
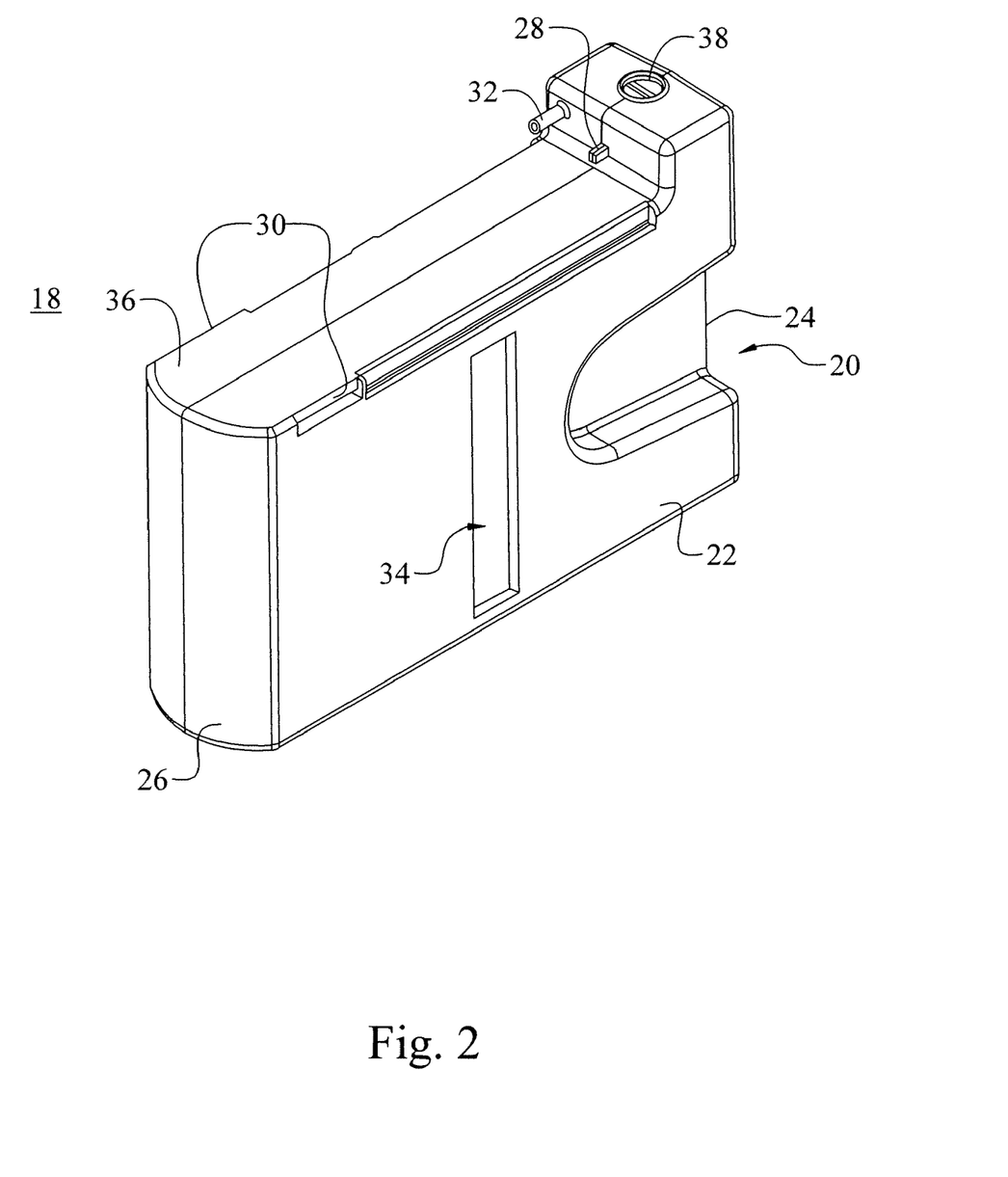
FIG. 2 is a perspective view of a portion of an ophthalmic surgical cassette in accordance with the present invention.

Container 18 includes a top wall 36 having a first portion for receiving the irrigation and aspiration manifold base, a second portion having structure 32 for connection to an aspiration tube of the manifold, and structure 38 for connection to a venturi pump. Structure 38 typically is an orifice over which a gas is blown in order to create a venturi aspiration within the container 18.

Figure 3:
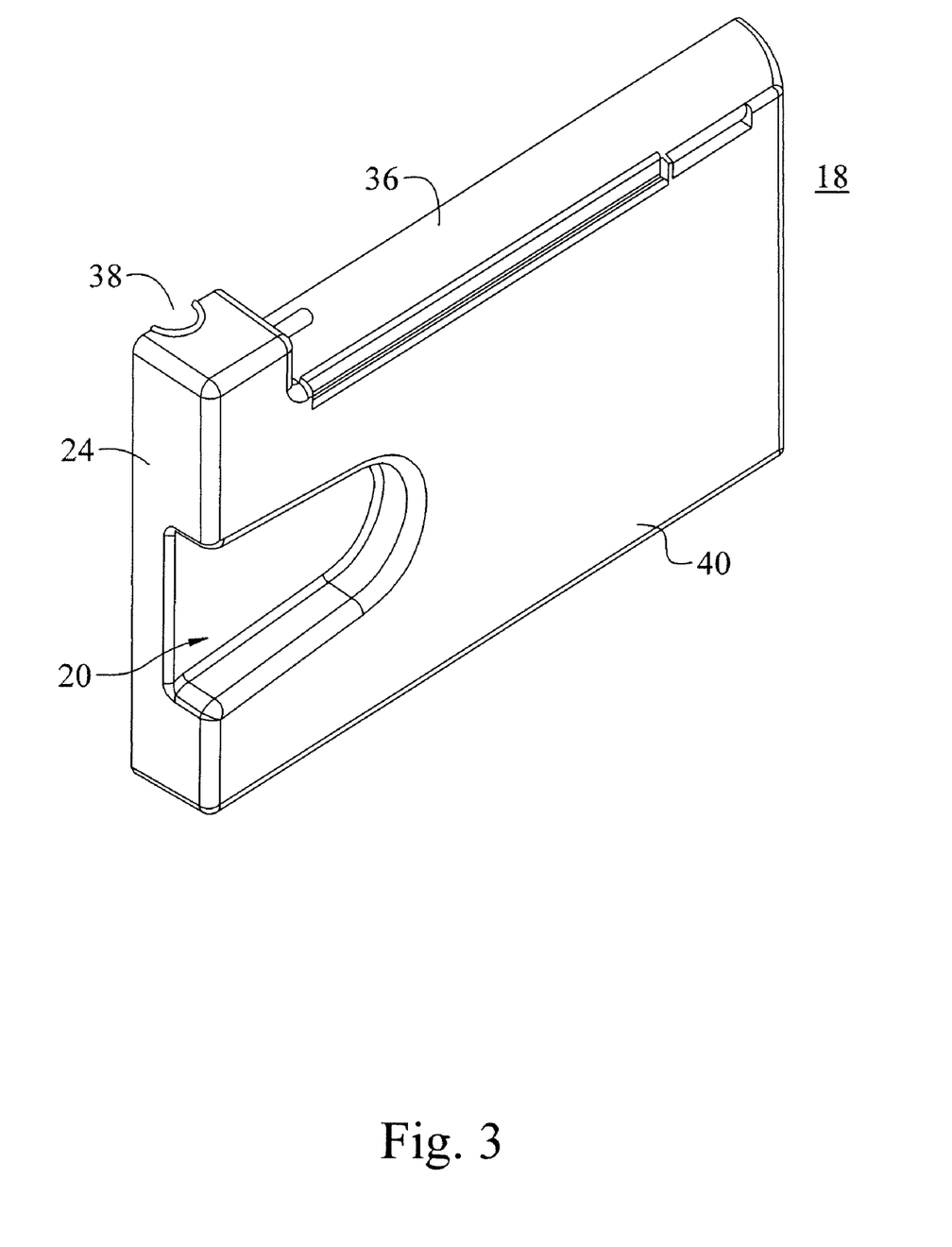
FIG. 3 is a cut-away partial view of FIG. 2.

Tapered slot 20 is preferably one of a pair of tapered alignment slots formed on opposing side walls of container 18. The slots preferably have a generally flared U-shape. These slots 20 assist a user in inserting the container 18 into pump 16 and ensure proper alignment of the container 18 within the pump 16. FIG. 3 shows a cut-away perspective view of container 18 that includes a side wall 40 on the opposite side from side wall 22. FIG. 3 also shows the additional preferred alignment slot 20 that is not shown in FIG. 2.

Figure 4:
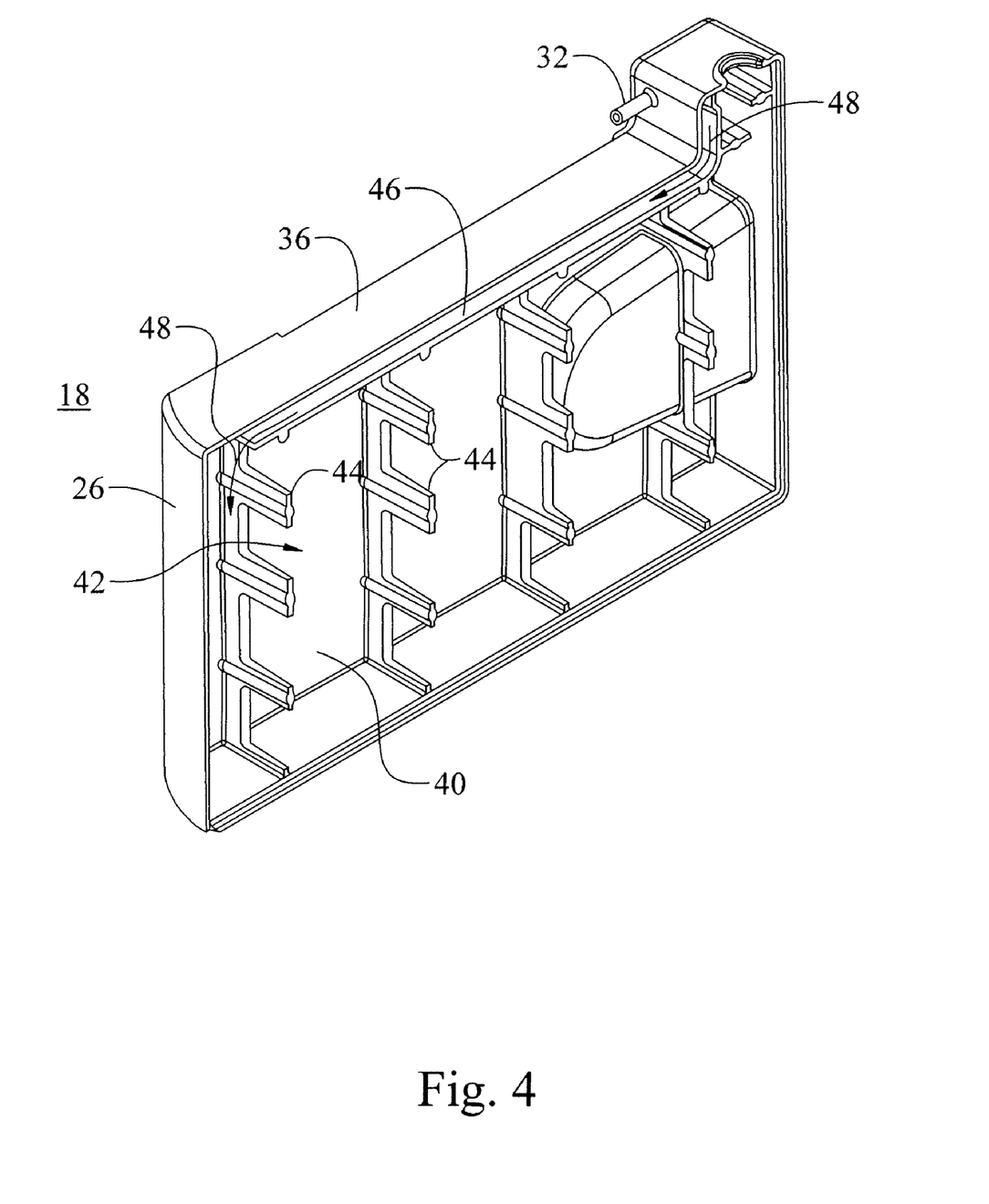
FIG. 4 is a perspective view of the opposite side of FIG. 3.

FIG. 4 shows a cut-away perspective view of the opposite side of the view shown in FIG. 3. FIG. 4 shows half of a majority of the interior volume of the container 18 at arrow 42. As can be seen, container 18 typically includes a plurality of rigid support members 44 spaced throughout container 18. These rigid supports 44 prevent the side walls 22 and 40 from collapsing when a vacuum is pulled within the interior volume 42 of container 18. An aspiration path is shown generally at 46, and aspirant fluid and tissue flow in the direction of arrows 48 within the container 18 for receiving aspirant fluid and tissue from an eye through inlet 32. Aspiration path 46 directs a flow of fluid towards a front half and preferably from a rear portion of the container 18 to adjacent front wall 26 of the container 18. The aspiration path 46, by directing the flow of fluid towards front wall 26, allows an operator to easily see if aspirant fluid and tissue is flowing into the interior volume 42 of container 18 during surgery. This is particularly advantageous because it provides a direct visual feedback to the operator that the aspiration of tissue is functioning properly during surgery. In this way, aspiration path 46, directs the flow of fluid towards a front half of container 18 before the fluid and tissue collects within a majority of the interior volume 42 of the container 18.

Figure 5:
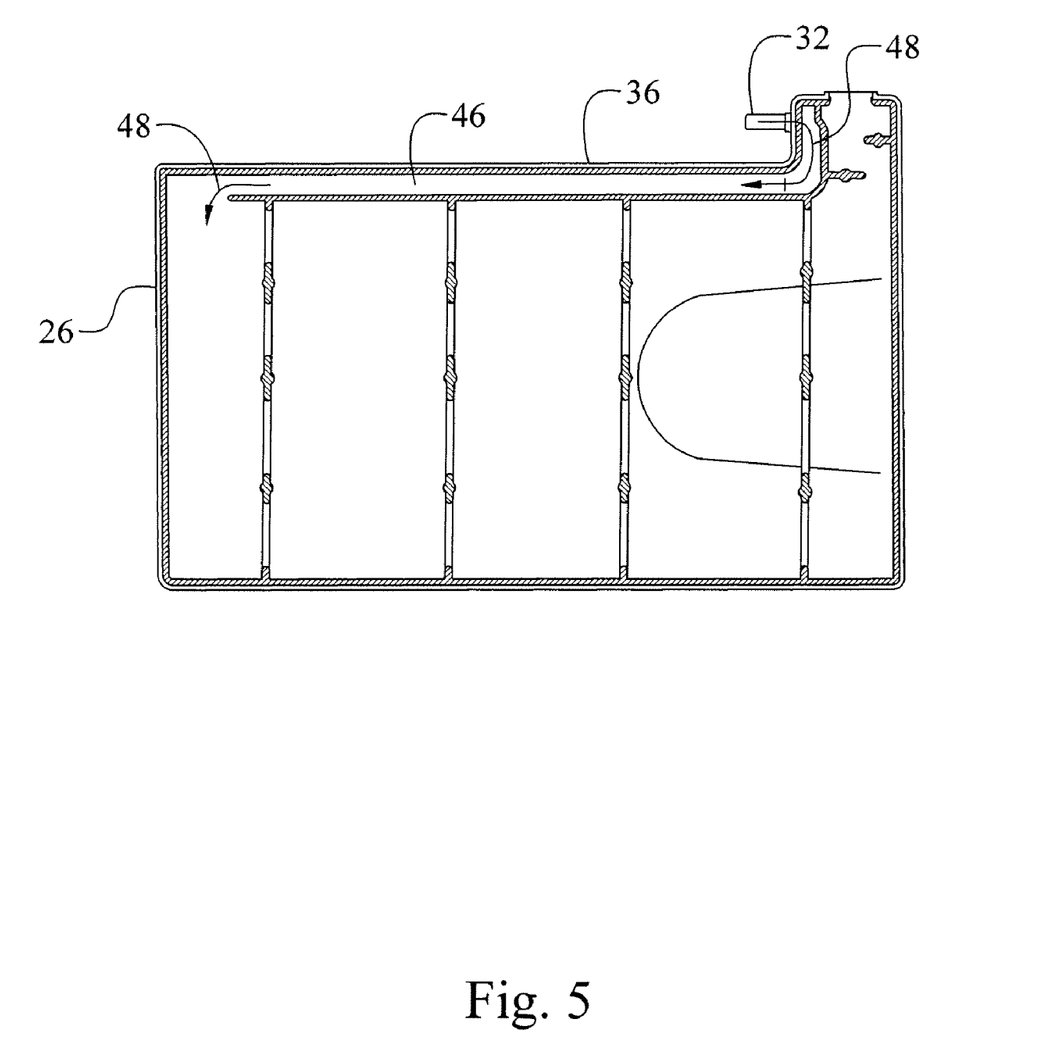
FIG. 5 is an elevational view of FIG. 4.

FIG. 5 is a plan elevation view of the perspective of FIG. 4, and more clearly shows the aspiration path 46 in the direction of fluid flow at arrows 48.

Figure 6:
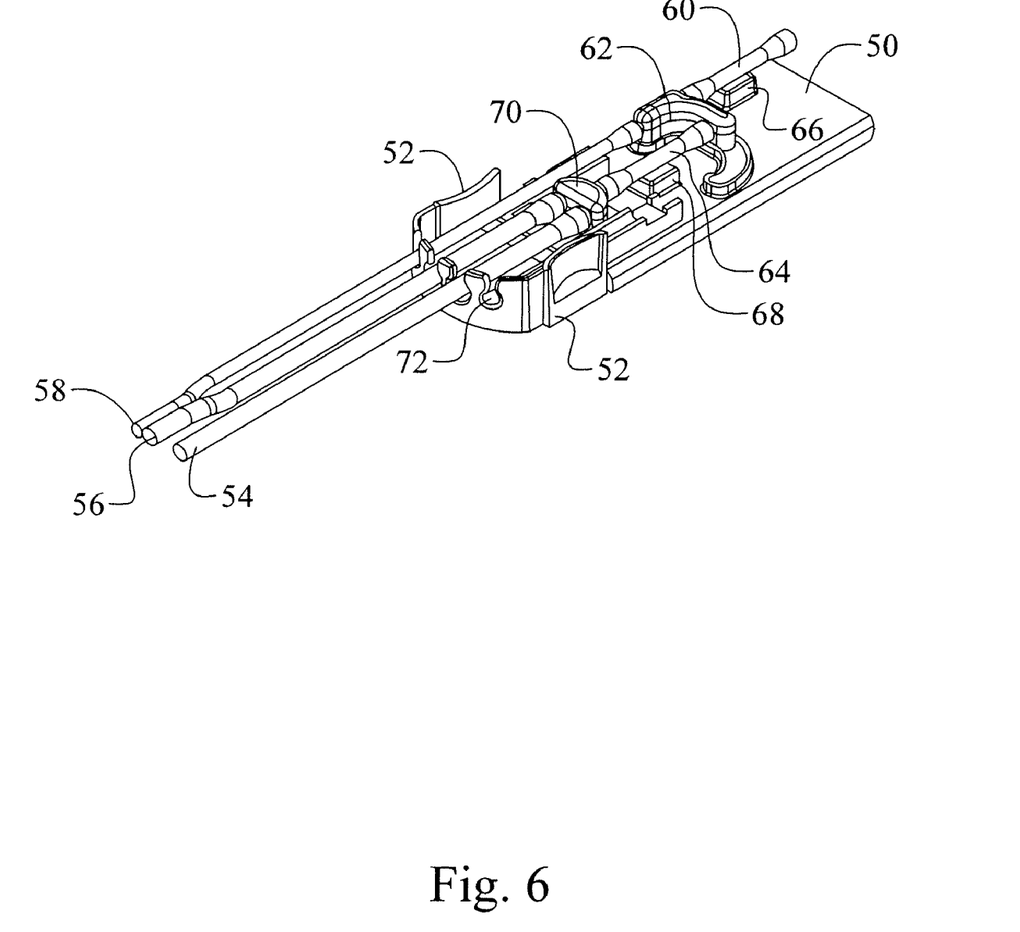
FIG. 6 is a perspective view of a portion of an ophthalmic surgical cassette in accordance with the present invention.

FIG. 6 shows a perspective view of a preferred embodiment of an irrigation and aspiration manifold base 50, in accordance with the present invention. Manifold base 50 includes tabs 52 that mate with notches 30, shown in FIG. 2, and base 50 also preferably fits between barb 28 and top surface 36, such that manifold base 50 is securely held on container 18. Manifold base 50 and container 18 combine to form an ophthalmic surgical cassette, in accordance with the present invention. Manifold base 50 preferably includes an irrigation inlet tube 54 for receiving irrigation flow from an irrigation source, such as is well known in the art. Manifold base 50 also preferably includes an irrigation outlet tube 56 for allowing irrigation fluid to flow from tube 54 into an ophthalmic surgical instrument for use during surgery. Manifold base 50 further preferably includes an aspiration line 58 and an aspiration tube 60 for delivering aspirant fluid and tissue from a surgical site (not shown) to container 18. Aspiration tube 60 is connected to inlet 32. Manifold base 50 also preferably includes aspiration manifold 62 which connects aspiration line 58 and aspiration tube 60 with reflux and liquid-vent tubing 64. Blocks 66 and 68 provide contact surfaces for conventional pinch valves to open and shut the reflux and vent tubing 64 and the aspiration line 60 and are controlled via pump 16 and surgical console 10 in a conventional manner. Irrigation inlet tubing 54 also preferably includes and cooperates with a pinch valve for turning irrigation fluid flow on and off. Irrigation manifold 70 connects reflux tubing 64 with irrigation inlet tubing 54 and irrigation outlet tubing 56. FIG. 6 shows manifold base 50 with an additional empty slot 72 which can be used for an alternate embodiment of the present invention, described in detail below at FIG. 8.

Manifold base 50 conveniently allows the irrigation inlet and outlet tubes 54 and 56 and the aspiration line 58 to remain connected to manifold base 50 as described above during an entire surgery. If container 18 were to fill with fluid and tissue and need to be emptied, a simple press of tabs 52 and a single disconnection of tube 60 from container 18 would allow an operator to empty container 18 and quickly reattach manifold base 50 to container 18 along with aspiration tube 60. In this manner, container 18 can be quickly and conveniently emptied without the clumsy and often times difficult removal of tubes 54, 56, and 58 as would be required in the prior art.

Figure 7:
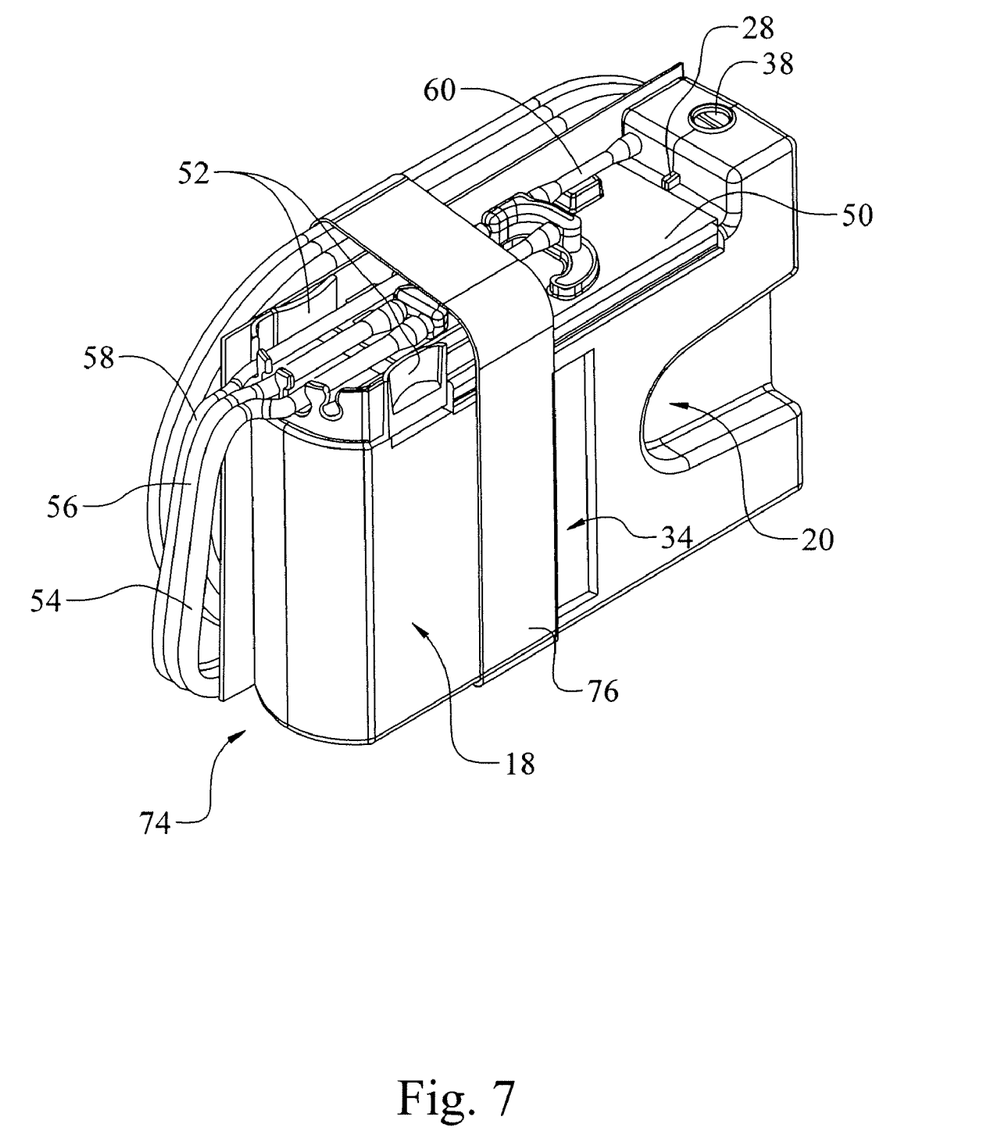
FIG. 7 is a perspective view of an ophthalmic surgical cassette in accordance with the present invention.

FIG. 7 is a perspective view of a cassette 74 in accordance with the present invention that includes container 18 and manifold base 50, as described above. Cassette 74 is shown with an entire length of tubing 54, 56, and 58 along with a retainer band 76 for inclusion within an ophthalmic surgical pack.

Figure 8:
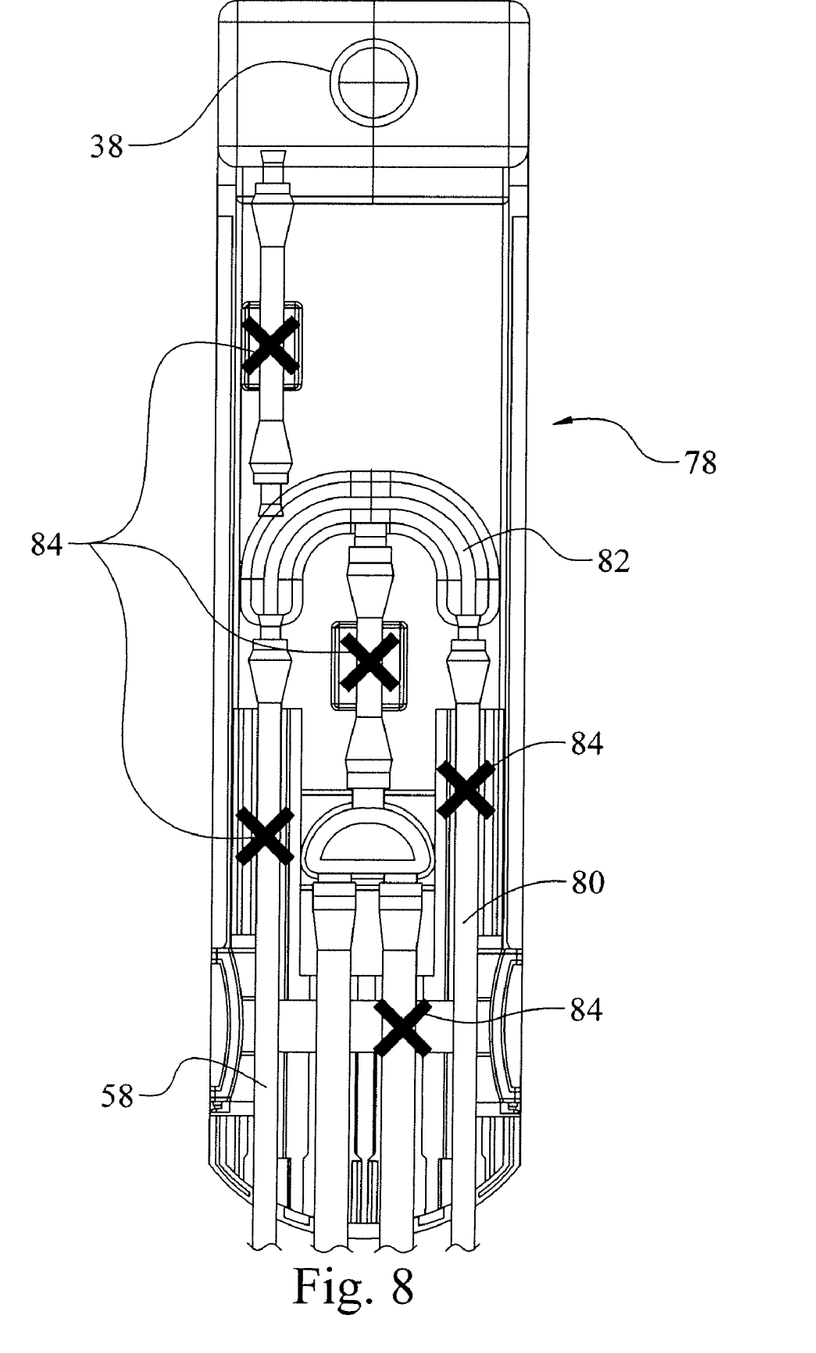
FIG. 8 is a top view of an alternate embodiment of FIG. 6.

FIG. 8 shows a top view of an alternate embodiment of a manifold base in accordance with the present invention. Manifold base 78 is identical to base 50 described above, with the exception that manifold base 78 preferably includes a second aspiration line or tube 80. Tube 80 is connected to an alternate embodiment of a manifold 82, which is similar to manifold 62 described above. Depending on the surgery performed, a surgeon may prefer a second aspiration line 80, as shown in FIG. 8 so that a second surgical handpiece can be attached without the need to remove the tubing from the surgical handpiece connected to aspiration line 58. FIG. 8 also conveniently shows preferred pinch valve locations as indicated by the dark "X"s at 84.

Figure 9:
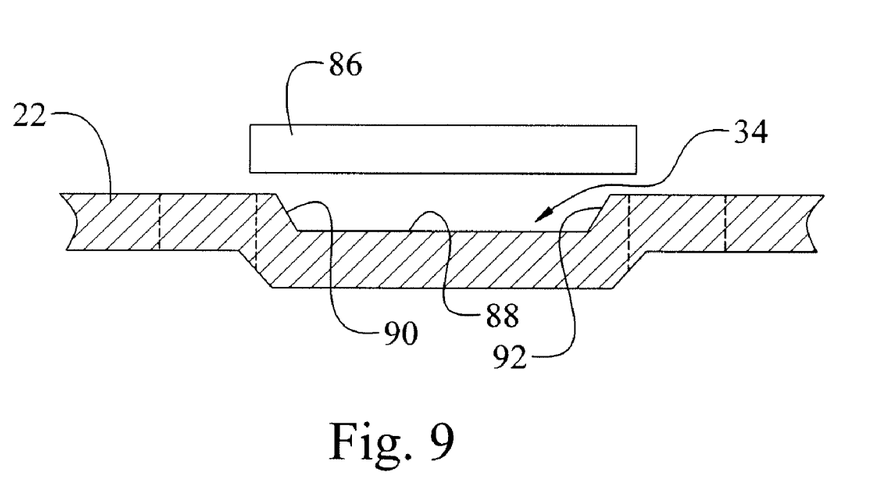
FIG. 9 is a partial cross-section of a portion of the cassette of FIG. 2.

FIG. 9 shows a partial cut-away cross-section of container 18 showing fluid level indicator 34 in cooperation with an associated photo-detector 86 of the pump 16. Fluid level indicator 34 is preferably formed on wall 22 of the container 18 such that associated photo-detector 86 of the pump 16 may determine a level of the fluid in the container. Fluid level indicator 34 essentially works as a prism to detect the fluid level in the container 18.

Fluid level indicator 34 is a notched section as shown having a face 88 essentially parallel to the wall 22 of the container 18 and a pair of angled side sections 90 and 92 connecting the face 88 to the wall 22 of the container 18, such that a prism is formed so that the fluid level of the cassette 74 can be determined by the photo-detector 86.

Photo-detector 86 could be an appropriate imaging device and lightsource, such as charge coupled devices (CCD) or CMOS devices or preferably could be a contact image sensor. A contact image sensor is essentially a one-dimensional array of photo-detectors used to create images. One example of a contact image sensor is Model M106-A6-R1 module available from CMOS Sensors Inc. Such contact image sensors are relatively small in size and are advantageous for use in the present invention. Though as stated above, other photo-detectors may be used in accordance with the present invention.

Figure 10:
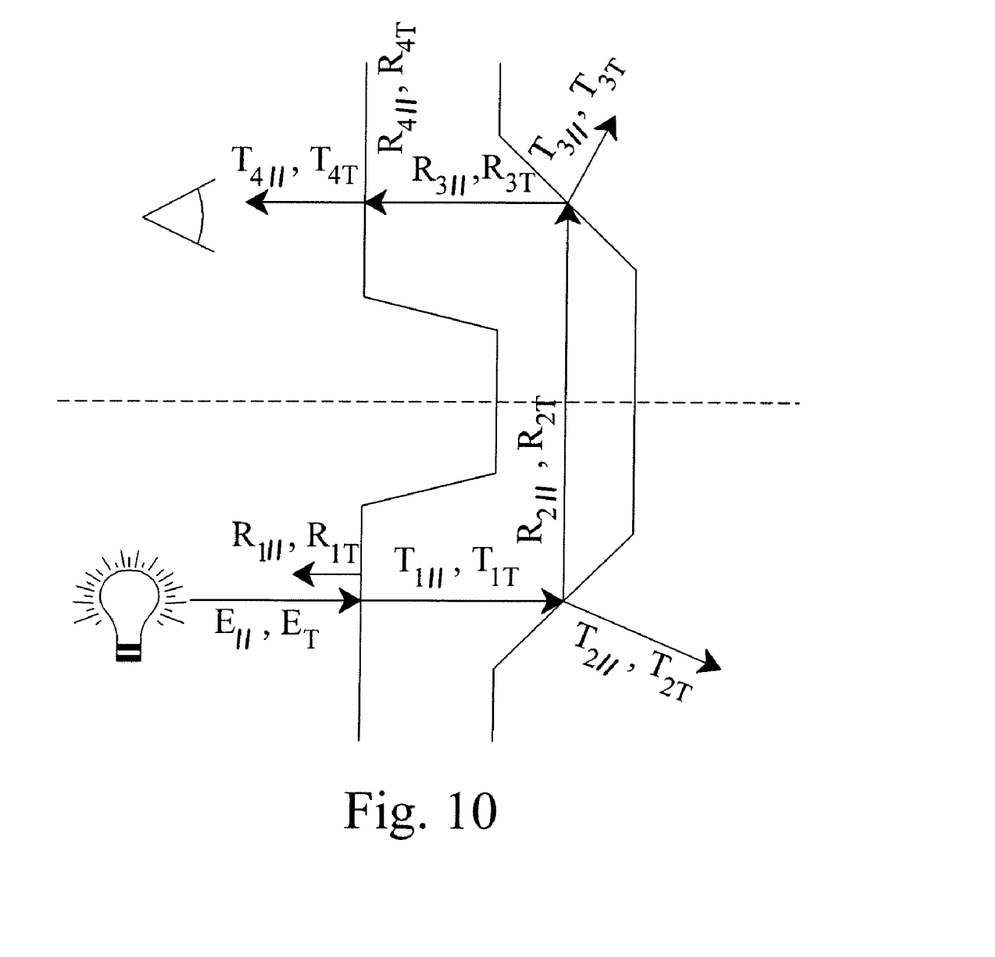
FIG. 10 is a graphical illustration of a detection scheme in accordance with the present invention.

FIG. 10 shows a light transmission diagram through a fluid level indicator, such as 34 (the prism of FIG. 10 is not drawn to the same scale as FIG. 9). Fluid level indicator 34 and photo-detector 86 cooperate to detect a fluid level through the physics of light transmission through a prism and between boundaries of materials having different indexes of refraction. As those skilled in the art will appreciate, when light intersects a boundary between two mediums at a right angle, almost all of the light is transmitted through the boundary. However, when light intersects a boundary between two mediums at an angle of less than 90°, some of the light is transmitted and some of the light is reflected. Both the angle of the light and the change in the index of refraction between the two mediums determines how much of the light is transmitted and how much of the light is reflected. This principle is applied to the present invention to detect the fluid level in the cassette 74. Detecting fluid level in cassette 74 with a photo-detector 86, such as a contact image sensor, includes two sets of boundary conditions. One set of boundary conditions is present below the fluid level and another set of boundary conditions exist above the fluid level. Both sets of boundary conditions have two interfaces. One interface is between air and the cassette material and the other is between the cassette material and the contents of the cassette, i.e., aspirant fluid and tissue or air. The first interface, between air and cassette material, is insignificant since the amount of light reflected will be the same independent of the contents of the cassette. The second interface, between the cassette material and the cassette contents is of most importance, since the amount of reflective light is directly related to the contents of the cassette. The various lines of FIG. 10 show this difference in reflected light.

Taking the reflected intensity concept described above one step further, by tailoring the reflection and the transmission coefficients, a greater difference between the fluid present and the fluid not present intensity can be achieved. This can be accomplished by molding features into the cassette wall, as described above in connection with FIG. 9. The amount of light received by the photo-detector 86 is directly proportional to the amount of light reflected at the medium boundaries. By monitoring the amount of light received at each of the photo-detectors, the fluid level can be determined. The fluid level will correspond to the point in which the intensity of the reflected light changes.

Figure 11:
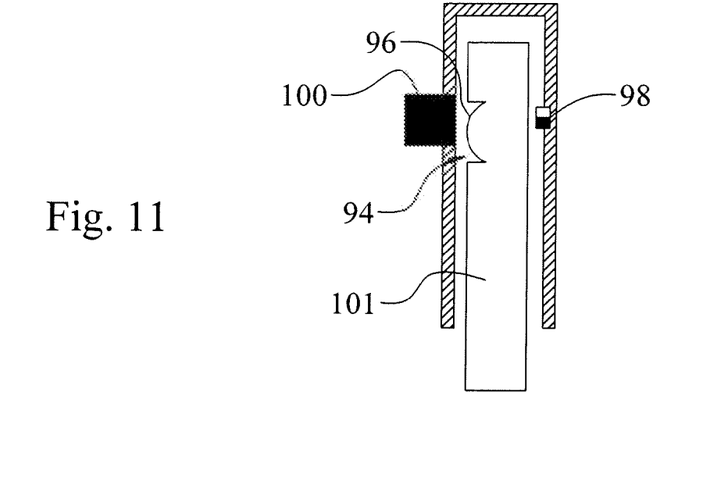
FIG. 11 is an alternate embodiment of a fluid level indicator in accordance with the present invention.
Figure 12:
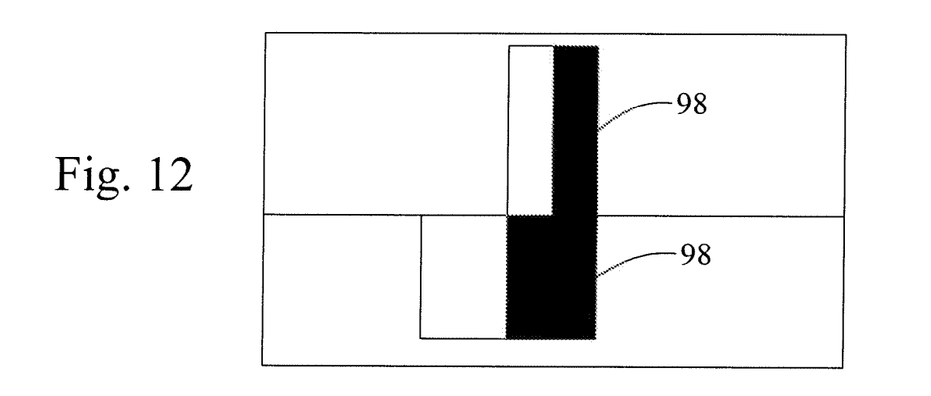
FIG. 12 is a graphical illustration of a fluid level detection of FIG. 11.
Figure 13:
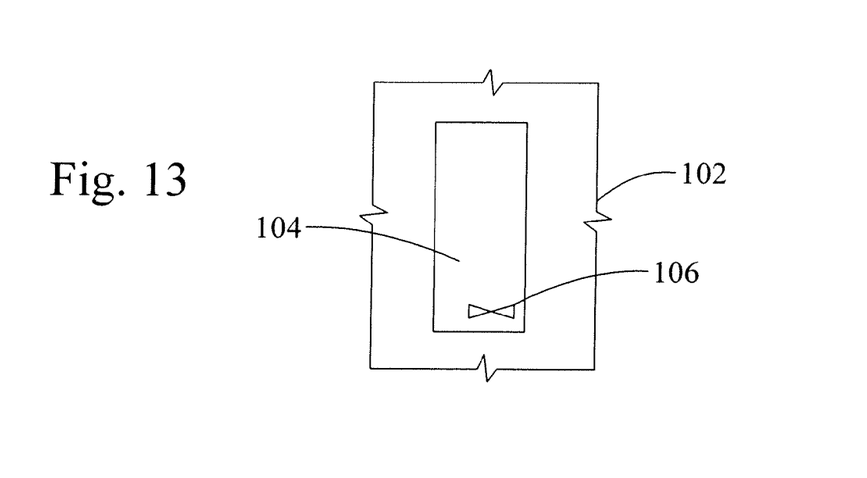
FIG. 13 is a cassette detection for use with a photo-detector in accordance with an alternate embodiment of the present invention.

FIGS. 11 and 12 show an alternate embodiment of a fluid level indicator, in accordance with the present invention. FIG. 11 shows a fluid level indicator 94 having a bulged area 96, such that the bulged area magnifies any fluid in the container, thereby allowing the photo-detector 100 to determine a fluid level of the cassette 101. Fluid level indicator 94 cooperates with contrasting colored strips 98, such that the bulged area 96 magnifies the strips 98 where fluid is present and does not magnify the strips where fluid is not present, as shown in FIG. 12. Photo-detector 100 then can determine the point at which the magnified strip changes to an unmagnified strip. Bulged area 96 is essentially a lens that takes advantage of the difference in indexes of refraction between air and fluid. In the embodiment of FIG. 11, if the cassette were to be molded with the bulged area 96, it would magnify an image, such as the strips 98 located on the opposite side of the cassette. FIG. 13 illustrates a further embodiment in accordance with the present invention. FIG. 13 includes a partial elevation view of a side wall 102 of a cassette similar to that described above and further includes a fluid level indicator 104 similar to indicator 34, described above. Indicator 104 further includes a geometric FIG. 106 or other indices, which can be used to identify the type of cassette to be used in surgery. This identification can be convenient for the system user, in that a posterior cassette could be distinguished from an anterior cassette and the proper surgical settings presented to the surgeon. The indice 106 is preferably positioned within indicator 104 at a point where fluid level detection is not needed.

Thus has been shown an inventive ophthalmic surgical cassette and system, variations of which will be apparent to those skilled in the art. Such variations are intended to be within the scope of the present invention and the claims set forth herein.

We claim:

1. A cassette for use with an ophthalmic surgery pump for collecting aspirant fluid and tissue from a patient's eye comprising:
   a rigid walled container having an interior volume for collecting the aspirated fluid and tissue;
   at least one tapered alignment slot formed in a side wall of the container and extending from a back wall towards a front wall;
   an irrigation and aspiration manifold base removeably attached to the container;
   an aspiration path formed within the container for receiving the aspiration fluid and the tissue from the eye and directing the flow of fluid towards a front half of the container before the fluid and tissue collects within a majority of the interior volume of the container; and
   a fluid level indicator formed on a wall of the container, such that an associated photo-detector of the pump may determine a level of fluid in the container.

2. The cassette of claim 1, wherein the container is formed of a transparent plastic material.

3. The cassette of claim 1, wherein the container includes a top wall having a first portion for receiving the irrigation and aspiration manifold base and a second portion having structure for connection to an aspiration tube of the manifold and structure for connection to a venturi pump.

4. The cassette of claim 1, wherein the cassette has a pair of tapered alignment slots formed on opposing side walls of the container.

5. The cassette of claim 4, wherein the slots have a generally flared U-shape.

6. The cassette of claim 1, wherein the manifold base further includes an infusion inlet tube, an infusion outlet tube, a fluid vent tube, and a first aspiration tube.

7. The cassette of claim 6, further including a second aspiration tube.

8. The cassette of claim 6, wherein the manifold base further includes an irrigation manifold connected to the infusion inlet tube, the infusion outlet tube, and the fluid vent tube, and an aspiration manifold connected to the first aspiration tube and the fluid vent tube.

9. The cassette of claim 7, wherein the aspiration manifold is further connected to the second aspiration tube.

10. The cassette of claim 1, wherein the aspiration path is formed from a rear portion of the container to adjacent a front wall of the container.

11. A cassette for use with an ophthalmic surgery pump for collecting aspirant fluid and tissue from a patient's eye comprising:
    a rigid walled container having an interior volume for collecting the aspirated fluid and tissue;
    an irrigation and aspiration manifold base removeably attached to the container for allowing the cassette to be emptied during surgery without disconnecting irrigation and aspiration tubes from the manifold base;
    wherein the container includes a top wall having a first portion for receiving the irrigation and aspiration manifold base and a second portion having structure for connection to an aspiration tube of the manifold and structure for connection to a venturi pump; and
    wherein the manifold base further includes an infusion inlet tube, an infusion outlet tube, a fluid vent tube, and a first aspiration tube.

12. The cassette of claim 11, further including a second aspiration tube.

13. The cassette of claim 11, wherein the manifold base further includes an irrigation manifold connected to the infusion inlet tube, the infusion outlet tube, and the fluid vent tube, and an aspiration manifold connected to the first aspiration tube and the fluid vent tube.

14. The cassette of claim 11, wherein the aspiration manifold is further connected to the second aspiration tube.

15. A cassette for use with an ophthalmic surgery pump for collecting aspirant fluid and tissue from a patient's eye comprising:
   a rigid walled container having an interior volume for collecting the aspirated fluid and tissue; and
   a fluid level indicator forming a part of a wall of the container, such that an associated photo-detector of the pump may determine a level of fluid in the container ; and
   wherein the fluid level indicator is a bulged area, such that the bulged area magnifies any fluid in the container, thereby allowing the photo-detector to determine a fluid level of the cassette.

* * * * *